United States Patent
Hatib et al.

(10) Patent No.: US 7,651,466 B2
(45) Date of Patent: Jan. 26, 2010

(54) PULSE CONTOUR METHOD AND APPARATUS FOR CONTINUOUS ASSESSMENT OF A CARDIOVASCULAR PARAMETER

(75) Inventors: Feras Hatib, Irvine, CA (US); Luchy Roteliuk, Lake Forest, CA (US); Jeffrey Pearce, Sultan, WA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1030 days.

(21) Appl. No.: 11/178,999

(22) Filed: Jul. 11, 2005

(65) Prior Publication Data

US 2006/0235323 A1    Oct. 19, 2006

Related U.S. Application Data

(60) Provisional application No. 60/670,767, filed on Apr. 13, 2005.

(51) Int. Cl.
*A61B 5/02* (2006.01)
(52) U.S. Cl. .................. 600/485; 600/526; 600/504; 600/483; 600/481
(58) Field of Classification Search ............ 600/481, 600/483–486, 488, 504–507, 526
See application file for complete search history.

(56) References Cited

U.S. PATENT DOCUMENTS 5,101,828 A    4/1992    Welkowitz et al.
(Continued)

FOREIGN PATENT DOCUMENTS

EP    1 103 217 A2    5/2001
(Continued)

OTHER PUBLICATIONS

Wesseling, K.H.; Jansen, J R C; Settels, J J; Schreuder, J J, Computation of Aortic Flow From Pressure in Humans Using a Nonlinear, Three-Element Model, Journal of Applied Physiology, May 1993, vol. 74, Nr. 5, pp. 2566-2573.
(Continued)

*Primary Examiner*—Charles A. Marmor
*Assistant Examiner*—Navin Natnithithadha
(74) *Attorney, Agent, or Firm*—Gregory J. Carlin

(57) ABSTRACT

A cardiovascular parameter such as cardiac output is estimated from a current pressure waveform data set without needing to directly measure blood flow or arterial compliance. The general shape of an input flow waveform over one beat-to-beat cycle is assumed (or computed), and then the parameters of a flow-to-pressure model, if not pre-determined, are determined using system identification techniques. In one embodiment, the parameters thus determined are used to estimate a current peripheral resistance, which is used not only to compute an estimate of the cardiovascular parameter, but also to adjust the shape of the input flow waveform assumed during at least one subsequent beat-to-beat cycle. Another embodiment does not require computation of the peripheral resistance and still another embodiment computes a flow estimate from an optimized identification of the parameters defining the assumed input flow waveform.

21 Claims, 5 Drawing Sheets

U.S. PATENT DOCUMENTS

| | | | |
|---|---|---|---|
| 5,183,051 | A | 2/1993 | Kraidin et al. |
| 5,241,966 | A | 9/1993 | Finkelstein et al. |
| 5,265,615 | A | 11/1993 | Frank et al. |
| 5,390,679 | A | 2/1995 | Martin |
| 5,400,793 | A | 3/1995 | Wesseling |
| 5,535,753 | A | 7/1996 | Petrucelli et al. |
| 5,647,369 | A | 7/1997 | Petrucelli et al. |
| 5,797,395 | A | 8/1998 | Martin |
| 5,913,826 | A | 6/1999 | Blank |
| 6,027,453 | A * | 2/2000 | Miwa et al. ............. 600/485 |
| 6,027,455 | A * | 2/2000 | Inukai et al. ............. 600/490 |
| 6,036,651 | A * | 3/2000 | Inukai et al. ............. 600/485 |
| 6,036,652 | A * | 3/2000 | Inukai et al. ............. 600/493 |
| 6,348,038 | B1 | 2/2002 | Band et al. |
| 6,485,431 | B1 | 11/2002 | Campbell |
| 6,527,725 | B1 * | 3/2003 | Inukai et al. ............. 600/485 |
| 2004/0158163 | A1 * | 8/2004 | Cohen et al. ............. 600/508 |

FOREIGN PATENT DOCUMENTS

| | | |
|---|---|---|
| WO | WO 92/06633 | 4/1992 |
| WO | WO 92/01804 | 7/1992 |
| WO | WO 97/24982 | 7/1997 |
| WO | WO 97/47236 | 12/1997 |

OTHER PUBLICATIONS

Guido Avanzolini, Paolo Barbini, Tracking Time-Varying Properties of the Systemic Vascular Bed, Ilee Transactions On Biomedical Engineering, Mar. 1989, vol. 36, No. 3.

A. S. Ferreira, J. Barbosa Filho, M.N. Souza, Identification of Vascular Parameters Based on the Same Pressure Waves Used to Measure Pulse Wave Velocity, 2001 Proceedings of the $23^{rd}$ Annual EMBS International Conference, Oct. 25-28, Instanbul, Turkey, Oct. 2001, 4 pages.

Office Action, P.R. China, Apr. 3, 2009.

Avanzolini, et al., Tracking Time-Varying Properties of the Systemic Vascular Bed, IEEE Transactions on Biomedical Engineering USA, vol. 36,3, Mar. 31, 1989, pp. 373-381.

Maurice J. Bourgeois "Continuous Determination of Beat-to-Beat Stroke Volume from Aortic Pressure Pulses in the Dog" Circulation Research vol. 39, No. 1, Jul. 1976.

Maurice J. Bourgeois, "Characteristics of Aortic Diastolic Pressure Decay with Application to the Continuous Monitoring of Changes in Peripheral Vascular Resistance" Circulation Research vol. 35, Jul. 1974.

Bruce A. McKilnley "Tissue Hemoglobin $O_2$ Saturation during Resuscitation of Traumatic Shock Monitored Using Near Infrared Spectrometry" Journal Of Trauma: Injury, Infection, And Critical Care, vol. 48, No. 4, Apr. 2000.

J.R.C. Jansen "A comparison of cardiac output derived from the arterial pressure wave against thermodilution in cardiac surgery patients" British Journal of Anaesthesia 87(2):212-22 (2001).

Michael M. Hirschl "Noninvasive assessment of cardiac output in critically ill patients by analysis of the finger blood pressure waveform" Crit. Care Med. 1997 vol. 25, No. 11.

Salvatore M. Romano "Assessment of cardiac output from systemic arterial pressure in humans" Crit. Care Med. 2002 vol. 30, No. 8.

Timothy T. Hamilton "PulseCO: A Less-Invasive Method to Monitor Cardiac Output From Arterial Pressure After Cardiac Surgery", Ann. Thorac. Surg. 74:S1408-12 (2002).

Charles Weissman "Arterial Pulse Contour Analysis Trending Of Cardiac Output: Hemodynamic Manipulations During Cerebral Arteriovenous Malformation Resection" J. Clin. Monit. 1993:9:347-353.

G. Antonutto "Noninvasive assessment of cardiac output from arterial pressure profiles during exercise" Eur. J. Appl. Physiol. (1995) 72:18-24.

* cited by examiner

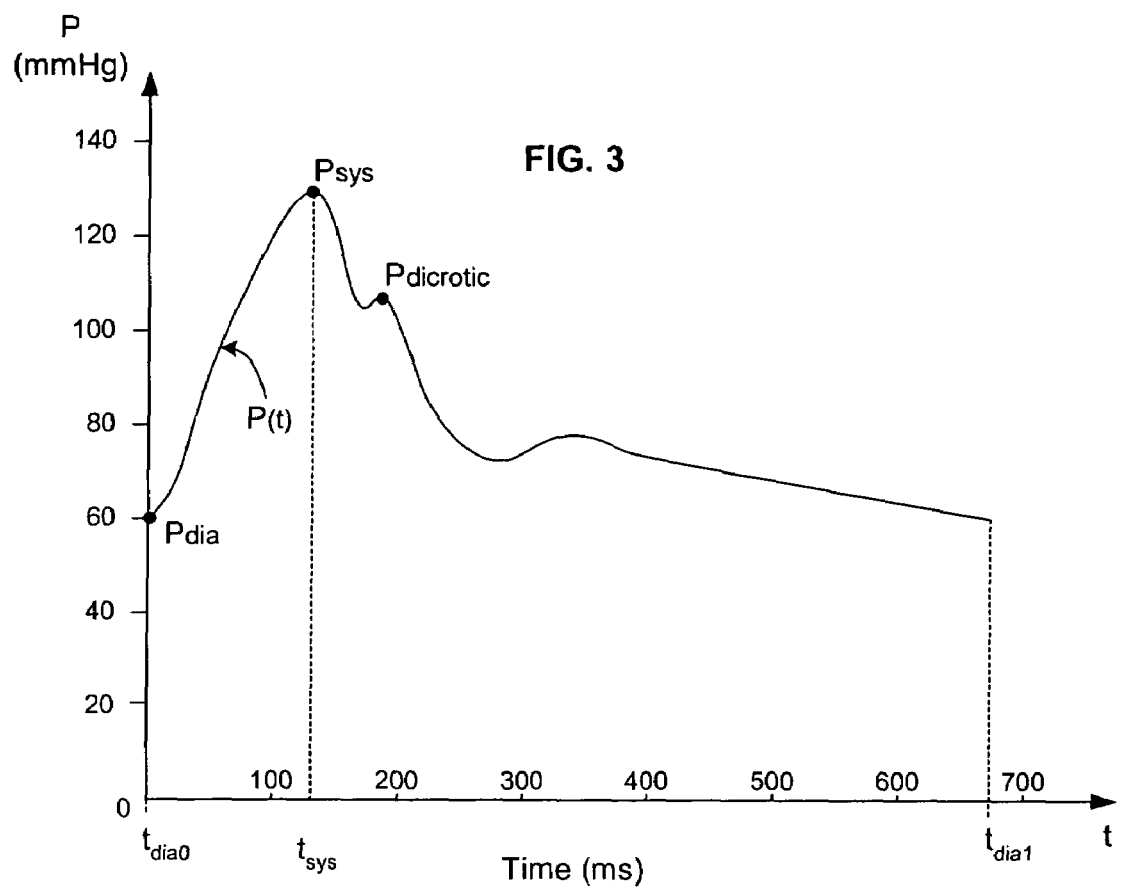
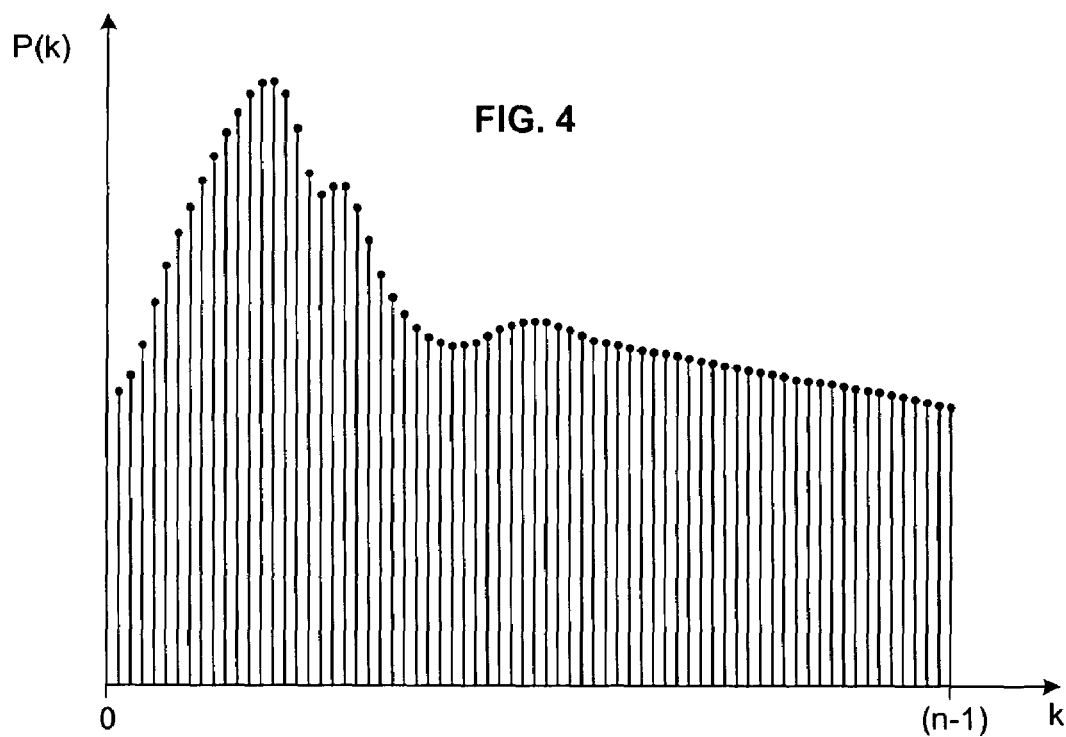

US 7,651,466 B2

PULSE CONTOUR METHOD AND APPARATUS FOR CONTINUOUS ASSESSMENT OF A CARDIOVASCULAR PARAMETER

CROSS-REFERENCE TO RELATED APPLICATIONS

This application claims priority of U.S. Provisional Patent Application No. 60/670,767, filed 13 Apr. 2005.

BACKGROUND OF THE INVENTION

1. Field of the Invention

This invention relates to a method for estimating a cardiovascular or hemodynamic parameter such as cardiac output (CO), as well as to a system that implements the method.

2. Background Art

Cardiac output (CO) is an important indicator not only for diagnosis of disease, but also for continuous monitoring of the condition of both human and animal subjects, including patients. Few hospitals are therefore without some form of conventional equipment to monitor cardiac output.

One basis for most common CO-measurement systems is the well-known formula CO=HR·SV, where SV is the stroke volume and HR is the heart rate. SV is usually measured in liters and HR is usually measured in beats per minute, although any other units of volume and time may be used. This formula simply expresses that the amount of blood the heart pumps out over a unit of time (such as a minute) is equal to the amount it pumps out on every beat (stroke) times the number of beats per time unit.

Since HR is easy to measure using any of a wide variety of instruments, the calculation of CO usually depends on some technique for estimating SV. Conversely, any method that directly yields a value for CO can be used to determine SV by division by HR. Of course, estimates of CO or SV can then be used to estimate, or contribute to estimating, any parameter that can be derived from either of these values.

One invasive way to determine cardiac output (or, equivalently, SV) is to mount some flow-measuring device on a catheter, and then to thread the catheter into the subject and to maneuver it so that the device is in or near the subject's heart. Some such devices inject either a bolus of material or energy (usually heat) at an upstream position, such as in the right atrium, and determine flow based on the characteristics of the injected material or energy at a downstream position, such as in the pulmonary artery. Patents that disclose implementations of such invasive techniques (in particular, thermodilution) include:

U.S. Pat. No. 4,236,527 (Newbower et al., 2 Dec. 1980);
U.S. Pat. No. 4,507,974 (Yelderman, 2 Apr. 1985);
U.S. Pat. No. 5,146,414 (McKown, et al., 8 Sep. 1992); and
U.S. Pat. No. 5,687,733 (McKown, et al., 18 Nov. 1997).

Still other invasive devices are based on the known Fick technique, according to which CO is calculated as a function of oxygenation of arterial and mixed venous blood. In most cases, oxygenation is sensed using right-heart catheterization. There have, however, also been proposals for systems that measure arterial and venous oxygenation non-invasively, in particular, using multiple wavelengths of light, but to date they have not been accurate enough to allow for satisfactory CO measurement on actual patients.

Invasive techniques have obvious disadvantages, the main one of which is of course that catheterization of the heart is potentially dangerous, especially considering that the subjects (especially intensive care patients) on which it is performed are often already in the hospital because of some actually or potentially serious condition. Invasive methods also have less obvious disadvantages: Some techniques such as thermodilution rely on assumptions, such as uniform dispersion of the injected heat, that affect the accuracy of the measurements depending on how well they are fulfilled. Moreover, the very introduction of an instrument into the blood flow may affect the value (for example, flow rate) that the instrument measures.

There has therefore been a long-standing need for some way of determining CO that is both non-invasive—or at least as minimally invasive as possible—and accurate. One blood characteristic that has proven particularly promising for accurately determining CO non-invasively is blood pressure.

Most known blood-pressure-based systems rely on the so-called pulse contour method (PCM), which calculates an estimate of CO from characteristics of the beat-to-beat pressure waveform. In the PCM, "Windkessel" (German for "air chamber") parameters (characteristic impedance of the aorta, compliance, and total peripheral resistance) are used to construct a linear or non-linear, hemodynamic model of the aorta. In essence, blood flow is analogized to a flow of electrical current in a circuit in which an impedance is in series with a parallel-connected resistance and capacitance (compliance).

FIG. 1 illustrates a classic two-element Windkessel model, in which Q(t) is the flow of blood from the heart to the aorta (or pulmonary artery); P(t) is the blood pressure in the aorta (or pulmonary artery) at time t; C is arterial compliance; and R is peripheral resistance in the systemic (or pulmonary) arterial system, all in suitable units. Assuming that the entire flow Q(t)=Q is constant and takes place only during systole, one obtains the following expression for P(t) during systole:

$$P(t) = R \cdot Q - (R \cdot Q - P_{ed}) \cdot e^{-t/\tau} \qquad \text{(Equation 1)}$$

where $P_{ed}$ is the end-diastolic pressure (diastolic pressure) and $\tau = R \cdot C$ is a decay constant. During diastole, Q(t)=0 (no inflow) and the expression for P(t) reduces to:

$$P(t) = P_{es} e^{-t/\tau} \qquad \text{(Equation 2)}$$

where $P_{es}$ is the end-systolic pressure.

The three required parameters of the model are usually determined either empirically, through a complex calibration process, or from compiled "anthropometric" data, that is, data about the age, sex, height, weight, etc., of other patients or test subjects. U.S. Pat. No. 5,400,793 (Wesseling, 28 Mar. 1995) and U.S. Pat. No. 5,535,753 (Petrucelli, et al., 16 Jul. 1996) are representative of systems that rely on a Windkessel circuit model to determine CO.

Many extensions to the simple two-element Windkessel model have been proposed in hopes of better accuracy. One such extension was developed by the Swiss physiologists Broemser and Ranke in their 1930 article "Ueber die Messung des Schlagvolumens des Herzens auf unblutigem Weg," Zeitung für Biologie 90 (1930) 467-507. FIG. 2 illustrates this model. In essence, the Broemser model—also known as a three-element Windkessel model—adds a third element (shown as resistance R0) to the basic two-element Windkessel model to simulate resistance to blood flow due to the aortic or pulmonary valve. It can be shown that the Broemser model reduces to the basic two-element Windkessel model under either of two circumstances: 1) R0=0; and 2) at diastole, when Q(t)=0 and dQ(t)/dt=0. Windkessel models having even more elements than three have also been proposed and analyzed.

PCM-based systems can monitor CO more or less continuously, with no need for a catheter to be left in the patient. Indeed, some PCM systems operate using blood pressure measurements taken using a finger cuff. One drawback of PCM, however, is that it is no more accurate than the rather simple, three-parameter model from which it is derived; in general, a model of a much higher order would be needed to faithfully account for other phenomena, such as the complex pattern of pressure wave reflections due to multiple impedance mis-matches caused by, for example, arterial branching. Other improvements have therefore been proposed, with varying degrees of complexity.

The "Method and Apparatus for Measuring Cardiac Output" disclosed by Salvatore Romano in U.S. Pat. No. 6,758,822, for example, represents a different attempt to improve upon PCM techniques by estimating SV, either invasively or non-invasively, as a function of the ratio between the area under the entire pressure curve and a linear combination of various components of impedance. In attempting to account for pressure reflections, the Romano system relies not only on accurate estimates of inherently noisy derivatives of the pressure function, but also on a series of empirically determined, numerical adjustments to a mean pressure value.

U.S. Published Patent Application No. 2004 0158163 (Richard J. Cohen, et al., 12 Aug. 2004, "Methods and apparatus for determining cardiac output") describes yet another technique for determining CO from the pulse pressure profile P(t). According to Cohen's method, the arterial blood pressure waveform (time profile) P(t) is measured over more than one cardiac cycle. For example, assume a pressure measurement taken over three cardiac cycles. The area under the pressure curve is then computed for each cardiac cycle. The pressure profile P(t) is also sampled ("digitized") to form a sequence of discrete values y(j) that represent P(t).

As is well known, the impulse response of any system is the function that describes how it acts (in reality or in a theoretical model) when it is subjected to an impulse of energy, force, etc. One step of Cohen's method involves creating a sequence of impulses x(k)—one at the beginning of each cardiac cycle—that has the same area as the "arterial pulse pressure." A second embodiment of Cohen's method involves creating a sequence of impulses x(k), each of which is located at the beginning of each cardiac cycle, with impulses that have equal areas but that are independent of the areas of the corresponding arterial pulse pressure waveforms. The values of x(k) and y(j) are then used in a convolution computation that models the cardiac system thus:

$$y(k) = \sum_{i=1}^{m} a_i \cdot y(k-i) + \sum_{i=1}^{n} b_i \cdot x(k-i) + e(k) \quad \text{(Equation 3)}$$

where e(t) is the residual error term, and m and n limit the number of terms in the model. The set of coefficients $\{a_i, b_i\}$ that optimizes the equation is then determined, for example, over 60-90 second intervals of x(k) and y(j), and by using least-squares optimization to minimize the residual error term e(t).

Given $a_i$ and $b_i$, Cohen then derives a single impulse response function h(t) that covers the entire multi-cycle measurement interval. It has long been known that the impulse response function of the heart usually takes the form, approximately, of a first-order exponential decay function. After an initial "settling" time of about 1.5-2.0 seconds, after which the effects of pressure reflections have mostly died out, Cohen then approximates h(t) from the expression:

$$h(t) = Ae^{\frac{-t}{\tau_D}} + w(t) \quad \text{(Equation 4)}$$

The parameters A (an assumed amplitude) and $\tau_D$ (the time constant) are then estimated from a minimization of the residual weight function w(t).

Cohen then computes CO, for example, from some variant of the formula:

$$CO = AC * ABP/\tau_D \quad \text{(Equation 5)}$$

where AC is a scaling constant and ABP is "arterial blood pressure," usually the average arterial blood pressure. The scaling factor AC can be determined using an independent calibration, and will either be, or at least be related to the arterial compliance value C. This is because, as is known:

$$CO = MAP/R \quad \text{(Equation 6)}$$

where MAP is the mean arterial pressure, which in most cases will be the same as Cohen's term ABP. Equation 5 transforms into Equation 6 if AC=C, since $\tau_D = R*C$.

One weaknesses of the approach disclosed by Cohen is that it requires determination of the scaling, that is, calibration factor AC, or, equivalently, determination of C. Accuracy of the CO measurement is therefore closely dependent on the accuracy of the calibration or compliance calculation. Another weakness of Cohen's method is that the recursive expression (Equation 3) used assumes a constant input amplitude and therefore fails to determine the proper d.c. offset. This in turn causes an even greater reliance on accurate determination of AC (or C).

Still another disadvantage of Cohen's approach is that it ignores much of the information contained in the pressure waveform—indeed, one embodiment of Cohen's method uses only a single characteristic of each waveform, namely, the area, when constructing the impulses x(k). In a second embodiment of Cohen's method, the information contained in the pulse pressure waveform is totally ignored. Cohen compensates for this in part by evaluating many pressure waveforms at a time—for example, Cohen's preferred embodiment monitors CO by analyzing "long time scale variations (greater than a cardiac cycle) in a single ABP signal" and determines $\tau_D$ "through the analysis of long time intervals" 60-90 seconds long. Another consequence of Cohen's greatly simplified input signal x(t) is the need for a complicated transfer function model (see Equation 3), which involves many zeroes, many poles, and, consequently, design and computational complexity.

What is needed is a system and method of operation for estimating CO, or any parameter that can be derived from or using CO, that is robust and accurate and that is less sensitive to calibration errors. This invention meets this need, and, indeed, provides an advantageous method and system for estimating even other cardiovascular parameters.

SUMMARY OF THE INVENTION

The invention provides a processing system, and a related method of operating it, for determining a cardiovascular parameter, for example, cardiac output (CO), blood flow, stroke volume, or a value that can be derived from any of these. A current pressure waveform data set corresponding to arterial blood pressure is input to the processing system over at least one current pressure cycle; both invasive and non-invasive blood pressure-measuring devices may be used. The defining parameters of an assumed, non-impulsive input flow waveform are then determined as a function of a peripheral resistance value determined for at least one previous pressure cycle, at least one shape-characterizing value in the current pressure waveform data, or both. For example, the defining parameters may be computed so as to form a function that, when transformed according to the cardiovascular model, most closely yields the current pressure waveform data set in a predetermined sense One of several examples of a shape-characterizing value is the time from the onset of systole to a time at or near systole, which, in some embodiments of the invention, is used together with the difference in pressure at these two times. The model parameters of a flow-to-pressure cardiovascular model are also determined, if they are not given. Examples of such a model include a discrete, auto-regressive representation of a multi-element Windkessel model of the aorta, in which case the model parameters are coefficients of the discrete, auto-regressive representation. An estimate of the cardiovascular parameter is then computed as a function of the determined model parameters.

The assumed input flow waveform is advantageously a series of assumed input waveform components. Examples of such waveform components include square waves, saw tooth waves, polynomials, piecewise linear functions, one or more Bezier curves, one or more sinusoidal component curves, etc.

In one embodiment of the invention, in which the input flow waveform components are determined as a function of a peripheral resistance value, a diastolic time constant is estimated as a product of a sampling rate at which the pressure waveform data set is derived and a function of a model feedback parameter; an arterial compliance value is estimated as a ratio of the diastolic time constant and the peripheral resistance value; a systolic time constant is estimated from chosen points in the current pressure waveform data set; an aortic characteristic resistance value is computed as a ratio of the systolic time constant and the arterial compliance value; and the amplitude of the component waveform for the current pressure cycle is set to be inversely proportional to the square of a function of at least one aortic characteristic resistance value.

In a particular version of this embodiment, the mean of a plurality of aortic characteristic resistance values is computed, which will include at least one aortic characteristic resistance value estimated for a previous cycle, and the amplitude of the component waveform for the current pressure cycle is set to be inversely proportional to the square of the product of the mean and a calibration constant and, optionally, the arterial compliance value. Where the input waveform components are primarily characterized by an amplitude and a duration, the amplitude of the component waveform for the current pressure cycle may similarly be set to be proportional to a peak-to-peak value of the current pressure waveform data set and inversely proportional to a function of the current peripheral resistance value, such as a mean value of a plurality of previously estimated peripheral resistance values. The amplitude may optionally be scaled by a calibration constant.

In one embodiment, cardiac flow is estimated as a function of the assumed input flow waveform. Cardiac stroke volume may then be estimated by integrating the assumed input flow waveform over at least one pressure cycle. The model parameters may be determined either independently, or be predetermined or computed independent of the current pressure waveform data set, or computed at the same time as the defining parameters of the assumed input flow waveform in a single optimization.

BRIEF DESCRIPTION OF THE DRAWINGS

FIG. 3 is an illustrative example of a complex blood pressure curve over one beat-to-beat heart cycle.

FIG. 4 illustrates a discrete-time representation of the pressure waveform in FIG. 3.

DETAILED DESCIRIPTION

Figure 1:
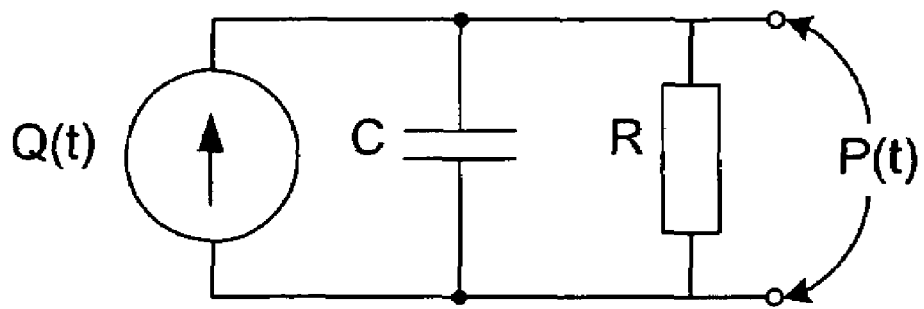
FIG. 1 illustrates a two-element Windkessel model, which is often used as the basis of the pulse contour method for estimating cardiac output.

In broadest terms, the invention involves a new pulse contour method and system implementation for continuous assessment of cardiac output (or of any value that can be derived from a cardiac output estimate) from peripheral blood pressure. In general, the invention posits an assumed, non-impulsive input flow waveform, at least one of whose defining parameters is a function of at least one value of an input pressure waveform data set, and which is then used in a system-identification routine to determine the parameters of a model of the relationship between input flow and output pressure. Parameters characterizing the relationship are then used to compute an estimate of the cardiovascular parameter of interest.

The primary exemplifying embodiment of the invention described below uses an autoregressive algorithm to compute values of the arterial compliance and the peripheral resistance. The invention then applies these values to the model as well. The following discussion focuses primarily on the preferred embodiment of the invention, since doing so also makes clear the important generally applicable aspects of the invention, but various alternatives are also described.

The invention may be used to advantage with any type of subject, whether human or animal. Because it is anticipated that the most common use of the invention will be on humans in a diagnostic setting, the invention is described below primarily in use with a "patient." This is by way of example only, however—it is intended that the term "patient" should encompass all subjects, both human and animal, regardless of setting.

Because of its clinical significance, it is anticipated that most implementations of the invention will generate cardiac output (CO) estimates—either as an end result or as an intermediate result used for calculating for CO-related value—based on measurements of systemic arterial blood pressure. It would also be possible to use measurements of blood pressure taken elsewhere, however, such as in the pulmonary artery on the right side, although such sites may require invasive intracardiac measurement. Moreover, another embodiment of the invention is described below in which the (or another) cardiovascular value of interest is flow or stroke volume, in which case there may be no need to calculate a CO estimate at all, or to do so as a separate calculation.

The system according to one embodiment of invention implements three main steps: 1) it generates an assumed input waveform, which comprises a train of assumed input waveform components, and which closely approximates the beat-by-beat blood flow signal, which is preferably based on an acquired arterial blood pressure signal and past estimated values of the arterial compliance and the peripheral resistance; 2) it uses the generated assumed input waveform and the acquired peripheral arterial pulse pressure signal to estimate the arterial compliance and the peripheral resistance with a system identification approach relative to a model of the flow/pressure system; and 3) it uses the estimated arterial compliance and peripheral resistance values to generate the assumed input waveform component for the next time interval and calculate a CO estimate.

Arterial compliance and peripheral resistance may thus be estimated continuously based on a recursive system identification approach, in which the current computed values are used to estimate the blood flow of the next time interval. For the first time interval at the start, reasonable initial values may be assumed. Over the next time intervals, this embodiment of the invention converges to the proper mean values of the arterial compliance and the peripheral resistance. The invention enables continuous CO monitoring from the peripheral blood pressure waveform.

Pressure Waveforms

FIG. 3 illustrates an example of a waveform P(t) of arterial pressure taken over a single heart cycle, here, from the point of diastolic pressure $P_{dia}$ at time $t_{dia0}$, through the time $t_{sys}$ of systolic pressure $P_{sys}$, to a time $t_{dia1}$ at which the blood pressure once again reaches $P_{dia}$.

According to the invention, P(t), or any signal that is proportional to P(t), may be measured at any point in the arterial tree, either invasively or non-invasively. If invasive instruments are used, in particular, catheter-mounted pressure transducers, then any artery may be used as a measurement point. Placement of non-invasive transducers will typically be dictated by the instruments themselves—the placement of finger cuffs, upper arm pressure cuffs, and earlobe clamps should be obvious. Regardless of the instrument, it will ultimately produce, or cause to be produced, an electric signal corresponding (for example, equal or just proportional) to P(t).

Rather than measure arterial blood pressure directly, any other input signal may be used that is proportional to blood pressure. Any needed scaling or conversion may then be done at any or all of several points in the calculations described below. For example, if some signal other than arterial blood pressure itself is used as input, then it may be calibrated to blood pressure before its values are used in the computations described below. In short, the fact that the invention may in some cases use a different input signal than a direct measurement of arterial blood pressure does not limit its ability to generate an accurate CO estimate. The only requirement of this invention is that a signal or data set equal or at least having a known relationship to (such as being proportional to) the patient's blood pressure over the interval of interest (including continuously) must be made available to the processing system (see below) that carries out the signal conditioning and various calculations described below.

As is well known, and as is illustrated in FIG. 4, analog signals such as P(t) can be digitized into a sequence of digital values using any standard analog-to-digital converter (ADC) with a sampling period of $t_s$. In other words, P(t), t0≦t≦tf, can be converted, using known methods and circuitry, into the digital form P(k), k=0, (n−1), where t0 and tf are initial and final times, respectively, of the computation interval and n is the number of samples of P(t) to be included in the calculations, distributed usually evenly over the computation interval.

Two-Element Windkessel Embodiment

As mentioned above, the invention takes a system identification approach relative to a model of the flow/pressure system. Prototypes of the invention that use various Windkessel models have been successfully tested, so the description of the invention found here concentrates primarily on embodiments of the invention that use system identification techniques based on different versions of Windkessel modeling. The general method according to the invention may be applied to implement many different systems for estimating CO using other models as well, however (including higher order models). The main requirement is that the model can be reduced to a discrete transfer function with parameters that can be determined through recursive comparison with the input signal model described below.

A first embodiment of the invention is based on the simple two-element resistance-capacitance electrical analog model of the arterial system, that is, the simple Windkessel model shown in FIG. 1. Recall that, in this model, the arterial compliance is represented by the capacitor C, and the peripheral resistance by the resistor R. The blood flow is modeled by the current Q(t), and the blood pressure P(t) is modeled by the voltage across the resistor R.

To carry out computations numerically and to estimate blood flow Q(t) (and subsequently CO) from the peripheral arterial pulse pressure P(t), values for the model parameters C and R must be known. The invention estimates the model parameters and the input flow Q(t) simultaneously based on a parametric autoregressive recursive approach.

The model shown in FIG. 1 has the following transfer function T(s) (from flow to pressure) in the s-domain:

$$T(s) = \frac{R}{1 + sRC} \quad \text{(Equation 7)}$$

Since the computations in a digital processing system are performed on the digitized blood pressure signals (that is, P(k) rather than directly on P(t)), the model must be converted to the digital domain (z-domain). To convert the model from continuous-time to discrete-time, the following approximation is used:

$$s \approx \frac{1 - z^{-1}}{t_s} \quad \text{(Equation 8)}$$

where $t_s$ is the sampling interval.

Substituting Equation 8 into Equation 7 yields the following discrete-time transfer function:

$$H(z) = \frac{R \cdot t_s}{t_s + \tau} \cdot \left( \frac{1}{1 - \frac{\tau}{t_s + \tau} \cdot z^{-1}} \right) \quad \text{(Equation 9)}$$

where τ=RC.

The transfer function of Equation 9 can be approximated by a first-order autoregressive model (AR model) having the following form:

$$\hat{H}(z) = \frac{b}{1 + a \cdot z^{-1}} \quad \text{(Equation 10)}$$

The coefficient b thus represents a feed-forward or d.c. gain factor and the coefficient a is a feedback gain factor.

Note the simplicity of this transfer function model, which has only a single pole, no zeroes, and corresponds to the "real life" Windkessel model. Although the method of this invention is not restricted to such a single-pole, no-zero transfer function model, this illustrates that such simplicity is possible using the invention, with accuracy that should be no less than that achieved by Cohen, and possibly even better. The inventors hypothesize that this is because the input model used in this invention incorporates more information about each cycle of pressure waveform that just its area.

Figure 5:
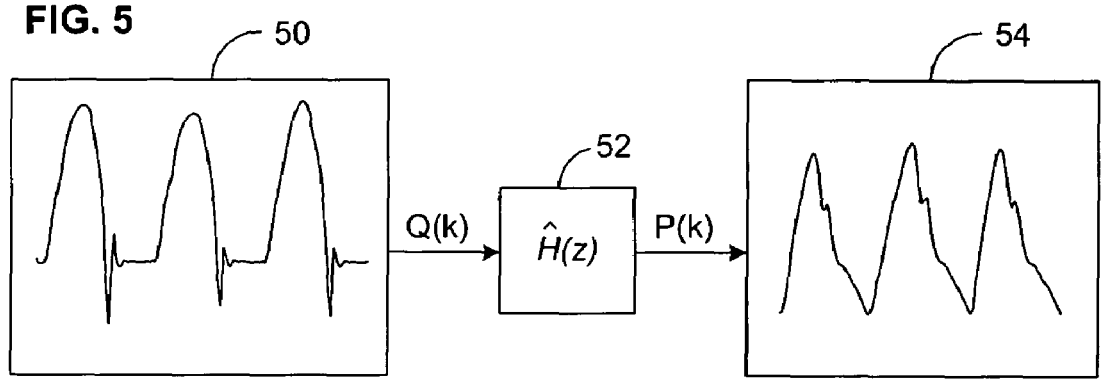
FIG. 5 illustrates the transfer function relationship between flow and pressure in the arterial system.

The model coefficients a and b in Equation 10 can be estimated using known parametric system identification methods. In order to apply a system identification approach however, both the input signal and the output signal of the system must be known. Given the system's transfer function, such as Equation 10, and an n'th estimate of the function's parameters (such as coefficients a and b), system identification routines typically generate an output signal (including waveforms) from the input signal and then compare this output signal with the actual, observed output signal, and either directly compute (if the function is simple enough) or, more often, iteratively adjust the coefficients until the difference between the generated and observed output signals is a minimum in some quantitative sense. In other words, these routines compute the values of the function's parameters that give a "best" match between the generated and observed outputs in any known sense. The coefficient values that give this best match are taken as the (n+1)'th estimate. Accordingly, in FIG. 5, the discrete flow (input) signal Q(k) is represented as waveform 50, the resulting discrete pressure (output) signal P(k) is represented by waveform 54, and the transform function relating the two is shown as module 52.

It is preferable to avoid the need for both a pressure and a flow transducer, however. Without actual knowledge of flow, only the output (the blood pressure signal) is assumed to be available to the system, with the system's input (blood flow) being unknown.

For this reason, instead of using an actual measured blood flow signal as the input for the system, the invention generates a train of assumed input waveform components Q(i) that is assumed to closely approximate it, with the time limits of each assumed input waveform component being related to known points of the sensed blood pressure waveform. The two key parameters in the construction of an assumed input waveform component as illustrated in the figures are its duration (the width) and its amplitude (the height). Note that the assumed input waveform components are not necessarily impulsive; in other words, each assumed input waveform component is defined by at least two parameters, such as amplitude and temporal width. Other parameters may include shape characteristics (such as for a square wave, triangular waves such as saw tooth waves, etc.); amplitude and frequency for each of a set of Fourier components; the m+1 coefficients of a polynomial of order m; the 8×n parameters of a set of n Bezier curves; the endpoints (or just the x- or y-coordinates of the endpoints) of segments of a piecewise linear approximating function, etc.

Figure 6:
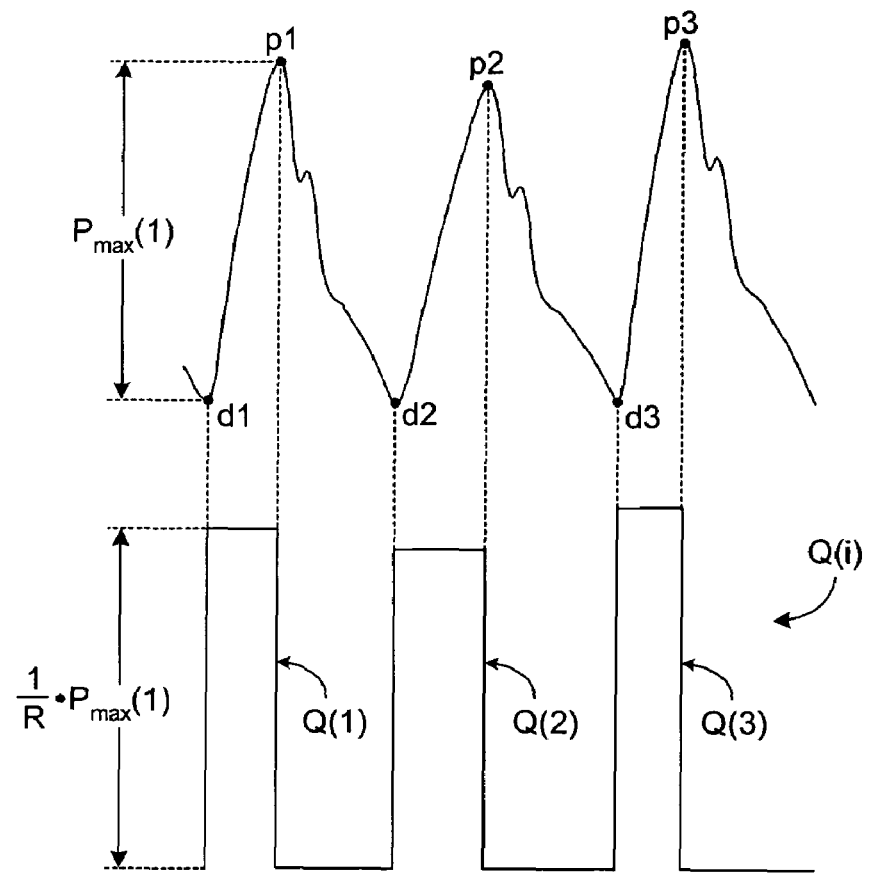
FIG. 6 illustrates how an input flow signal (waveform) is approximated as a sequence of input signal components derived from a sensed pressure waveform.

See FIG. 6. In the preferred two-element version of the invention, the duration of each current assumed input waveform component is set equal to the time interval between systole onset, that is, at or near diastole $P_{dia}$, and the location of the peak value, that is, at or near systole $P_{sys}$, of the pressure waveform in the current beat. Thus, the three assumed input waveform components Q(1), Q(2), and Q(3), in FIG. 6 extend temporally from the times of d1, d2, d3 to the times of p1, p2, p3, respectively.

According to Equation 7, the amplitude of the flow Q(t) is related to the arterial pulse pressure by a gain factor of R; therefore, the amplitude of the assumed input waveform, $Q_{max}(t)$, is best estimated by multiplying the peak-to-peak value of the arterial pulse pressure signal $P_{max}(t)$ by 1/R:

$$Q_{max}(t) = \frac{1}{R} \cdot P_{max}(t) \qquad \text{(Equation 11)}$$

To estimate the peripheral resistance R, the invention uses a parametric system identification approach, in which the coefficients a and b of Equation 10 are estimated using any known technique, such as least mean square regression. As is known, the way in which these routines work is to measure the difference between the observed output (pressure) waveform and the output (pressure) waveform that is produced by applying the transfer function with given parameters (a and b coefficients) to the assumed input waveform (Q(i)). The routine then iteratively (usually) adjusts the coefficients until a "best" fit is found according to some metric, such as least squares.

The input and the output of the system being identified are, respectively, the train of assumed input waveform components Q(i), which is taken to be an approximation of the flow signal Q(t), and the measured arterial pulse pressure P(t) (or, rather, its representation P(k)). Once the coefficients a and b are estimated, the invention can then calculate vascular resistance as follows:

$$R = \frac{t_s + \tau}{t_s} \cdot b \qquad \text{(Equation 12)}$$

where the time constant τ is estimated using the following equation:

$$\tau = \frac{a}{1-a} \cdot t_s \qquad \text{(Equation 13)}$$

The value of the peripheral resistance changes slowly from beat to beat; consequently, it will normally suffice to use a single value of R for an entire measurement interval of, for example, 15 or 30 s. The invention estimates R continuously, using a recursive approach: The current computed value of R is used to estimate the amplitude of each assumed input waveform component Q(i,k) in the train of assumed input waveform components Q(i) over the next time interval, and so on. The train of assumed input waveform components Q(i) is then used as the input for the system identification routine, which estimates the new coefficients a and b of the transfer function and therefore the new value of R. For the first time interval, that is, initially, any reasonable initial value of R may be assumed, and can be selected based on known properties of R, determined using well known laboratory methods, or in any other known manner. Over subsequent time intervals, the method converges to the proper value of R. For practical considerations, to reduce the effect of any variation in R and to ensure stability, instead of the previous value of R, the mean value of the N last time intervals may be used instead. Thus, for the n-th assumed input waveform, the amplitude of each waveform component Q(n,k) is estimated as follows:

$$Q_{max}(n, k) = \frac{1}{k_r \cdot \frac{1}{N} \sum_{p=n-N-1}^{p=n-1} R(p)} \cdot P_{max}(n, k) \qquad \text{(Equation 14)}$$

where $k_r$ is a constant reflecting the inaccuracies and the deviation of the assumed first-order AR model from the real arterial system.

So, at each iteration, the invention computes $Q_{max}(i,k)$ for each assumed input waveform component using the mean value of the N past values of R. Then, the train of assumed input waveform components Q(i) is generated with components having respective amplitudes $Q_{max}(i,k)$. The train of assumed input waveform components is then used to estimate the current value of R, for example, by using the approach of least-mean-square system identification applied to the model described by Equation 10. A CO value can then be computed using the well known formula:

$$CO = MAP/R \qquad \text{(Equation 15)}$$

where MAP is the mean arterial pressure and R is the current value of the peripheral resistance. MAP may be computed in any known way, for example, by taking the average of P(k) values over one or more cardiac cycles (that is, over one or more trough-to-trough or other periods of the discrete pressure waveform P(k)).

Notice that the invention estimates CO without needing to directly measure the model input signal, that is, the flow, and without needing to determine a compliance value C. Rather, an assumed input signal is used, and C is implicit in the time constant τ, which itself is implicit in the recursively estimated model coefficients a and b.

As illustrated in FIG. 6, each assumed input waveform component Q(i) is a simple square-wave. This has the advantage of computational simplicity and has proven in tests to be adequate. Moreover, even the square-wave assumed input waveform components described above contain information not only about the values and times of systole onset and peak pressure of the current waveform, but also of previous values of R; thus, compared with Cohen, the invention's assumed input waveform components encode much more information, and thus can rely on a less complicated (even single-pole, if desired) transfer function model.

A square-wave input signal is not necessary to the invention, however. Rather, other assumed input waveform component shapes could be used that more closely approximate the known profile of flow, such as is illustrated roughly in box 50 of FIG. 5. For example, a saw-tooth assumed input waveform component, full or half parabola, full or half sine wave, a composite sinusoidal waveform derived by Fourier analysis from know flow profiles, a polynomial approximation, etc., might better match the area under the portion of the flow waveform that corresponds to the time interval from the time of d1 to the time of p1. If such other assumed input waveform components are used, then skilled programmers, especially those with a background in numerical analysis and the design of time-series parameter identification methods, will know how to adjust the various optimization algorithms accordingly, for example, by including additional parameters relating, for example, to the shape or number of components in the approximating function for flow.

It would also be possible to perform the computations described here using the data from the input pressure waveform data set extending over more than one pressure cycle and, for example, to determine more than one assumed input waveform component at a time. Moreover, each assumed input waveform component could also be determined such that it is "wider" than what is illustrated in FIG. 6, that is, it need not end at the time at or near systole $P_{sys}$, but might even extend longer, even over each full cycle.

Three-Element Windkessel Embodiment

Figure 2:
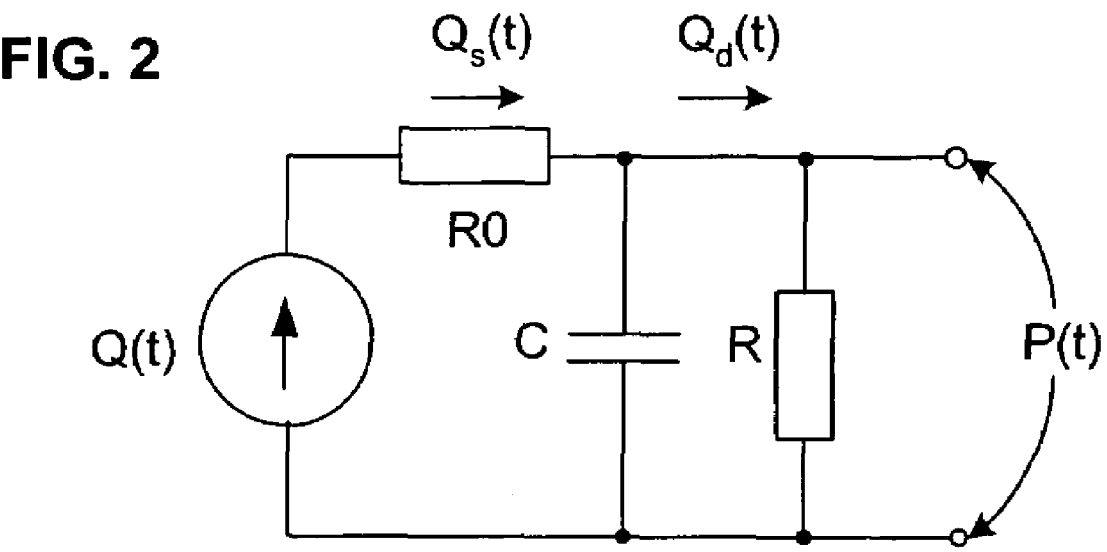
FIG. 2 illustrates the Broemser model, which is also known as a three-element Windkessel model
Figure 7:
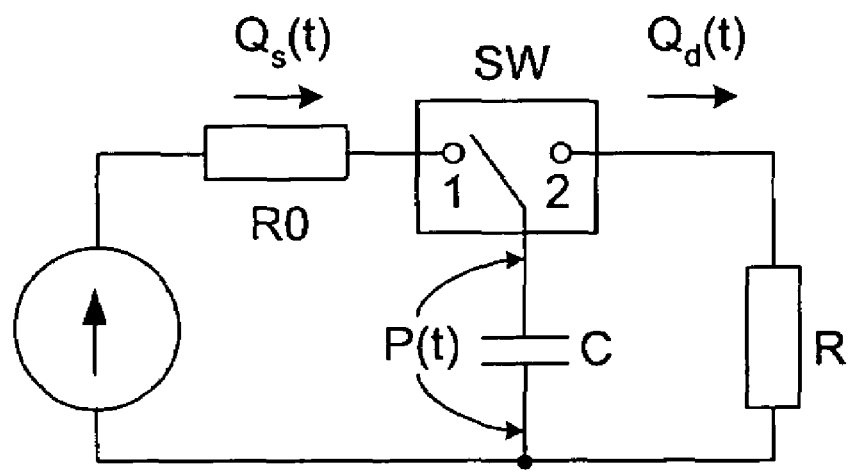
FIG. 7 illustrates a switched three-element Windkessel model used in one embodiment of the invention.

The second version of the method is based on the three-element analog model of the arterial system shown in FIG. 2. As explained above, the three elements of this model represent the three basic properties of the arterial system: R0—aortic characteristic resistance; C—vascular compliance; and R—peripheral resistance. As shown in FIG. 7, however, the model of the arterial system used in this embodiment of the invention also includes a single pole, double-throw switch SW in series between the resistance RO, and the parallel-connected capacitor C and resistance R. When the switch is in a first position (labeled 1), the capacitor C is charged by the current (aortic systolic inflow) $Q_s(t)(=Q(t))$ through the resistance R0. When the switch is in a second position, the capacitor C discharges with current (diastolic outflow) $Q_d(t)$ through the resistance R.

As in the two-element embodiment of the invention described above, to compute the input flow from the arterial pulse pressure, it is first necessary to estimate the values of the model parameters R0, C and R, either directly or implicitly. As did Wesseling this embodiment of the invention builds on the following assumptions: during systole (switch SW in position 1, the aortic systolic inflow ($Q_s$) is principally determined by the time constant $\tau_s = R0\ C$: the peripheral resistance R is not a major determinant of systolic inflow. During diastole (switch SW in position 2), this inflow is dissipated in the periphery. The diastolic outflow $Q_d$ and the pressure decay are essentially determined by the time constant $\tau_d = R\ C$. The compliance C is a common parameter in both time constants. This assumption is reasonable because it reflects the actual vascular physiological parameters: during systole the ventricle ejects blood into the compliant aorta. This blood is stored in systole, and, on elastic recoil in diastole, the peripheral vessels are perfused. In order to estimate the model's parameters R0, C and R the following approach is used:

In this aspect of the invention, the peripheral resistance R and the system's time constant τ are first estimated using the model of FIG. 1 and the recursive system identification routine described above (Equations 12 and 13) is executed. This is possible to do because, from the system identification point of view, the effect of R C is significantly greater than the effect of R0 C. This means that the time constant $\tau_d$ during diastole is significantly greater than the time constant $\tau_s$ during systole. Therefore, the results of the system identification estimation will reflect mainly the effects of R and C and the time constant τ estimated using system identification and Equation 13 is in fact the time constant during diastole $\tau_d$:

$$\tau_d = \frac{a}{1-a} \cdot t_S \qquad \text{(Equation 16)}$$

In this case, the peripheral resistance would be:

$$R = \frac{t_S + \tau_d}{t_S} \cdot b \qquad \text{(Equation 17)}$$

The train of assumed input waveform components needed for system identification is generated using a similar approach as before: Each assumed input waveform component Q(i,k) is located at the start of a systole of the blood pressure waveform and its width is set equal to the time interval between the systole onset and the location of the peak value of the pressure waveform in the current beat (between points di and pi in FIG. 6). The height (amplitude) of the component is defined by the three-element electrical model when the switch SW is in position 1 (FIG. 7):

$$Q_{max}(t) = \frac{1}{(R0 \cdot C)^2} \cdot P_{max}(t) \qquad \text{(Equation 18)}$$

In order to estimate R0, the invention uses the following approach: First the compliance C is estimated, using Equations 16 and 17:

$$C = \frac{\tau_d}{R} \quad \text{(Equation 19)}$$

R0 is then calculated:

$$R0 = \frac{\tau_s}{C} \quad \text{(Equation 20)}$$

Figure 8:
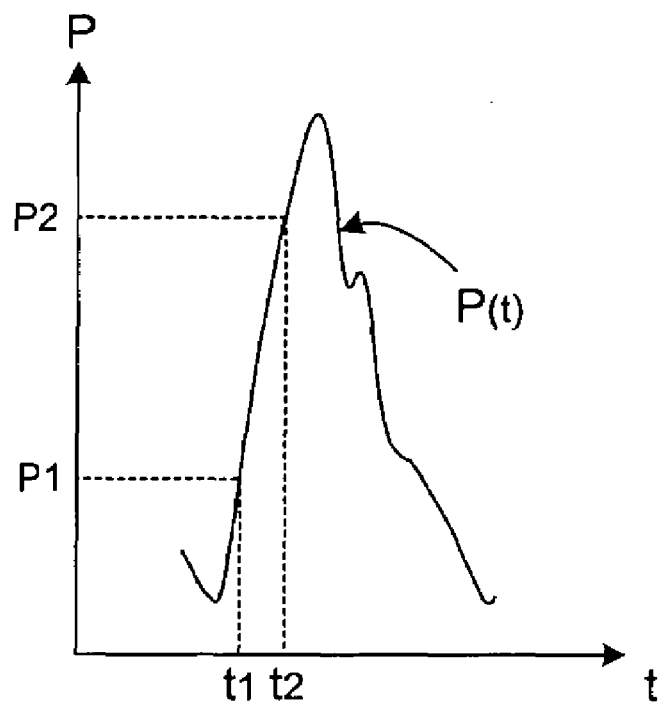
FIG. 8 illustrates how certain values are obtained from a current pressure waveform for use in CO estimation using the embodiment shown in FIG. 7.

The systolic time constant $\tau_s$ is estimated by selecting two points on the rising edge of the arterial pulse pressure waveform (for example, at 30% and 70% of the diastole level, respectively) as illustrated in FIG. 8, and then applying any known optimization routine to minimize the following function:

$$\min_{\tau_s} \left( P_1 - P_2 = P_1 e^{\frac{t_2}{\tau_s}} - P_2 e^{\frac{t_1}{\tau_s}} \right) \quad \text{(Equation 21)}$$

As in the previous case, the amplitudes $Q_{max}(i,k)$ of the individual assumed input waveform components are estimated using the mean value of R0 over the N last time intervals:

$$Q_{max}(n, k) = \frac{1}{\left( k_r \cdot \frac{1}{N} \cdot C \sum_{p=n-N-1}^{p=n-1} R0(p) \right)^2} \cdot P_{max}(n, k) \quad \text{(Equation 22)}$$

Cardiac output CO may then be calculated as before, that is, as in Equation 15.

Calibration

Both embodiments of the invention described above ultimately assume a determination of the $k_r$ constant in Equations 14 and 22. This is a calibration constant, which reflects the inaccuracies and the deviations due to the presumed first-order AR models of the arterial system.

The calibration constant $k_r$ could be estimated using, for example, a CO value measured by a bolus injection or any other "gold standard" method. In this case, the calibration could be done once for the current subject/patient at the start of the recording, and could remain effective for a long time afterward. Such embodiments of the invention can be termed "with-cal" embodiments in that they are provided with a value of $k_r$ that is obtained through external calibration. Experimental results and clinical studies using the invention show that the "with-cal" version of the algorithm offers both high accuracy and a very good trending of the estimated cardiac output.

As Equations 14 and 22 show, the calibration constant $k_r$ is within the recursion and therefore is affected by the feedback. The fact that calibration is done in the feedback loop, within the recursion and within the averaging, makes the algorithm less sensitive to the errors in the estimation of the calibration constant. In fact, the inventors have demonstrated experimentally that the error in the estimated CO value is proportional to the square root of the error in $k_r$. For instance, if the estimated $k_r$ deviates by 30% from the actual $k_r$, then this will cause a deviation of only 5.5% in the estimated cardiac output. This makes the invention more appropriate to use in either a "with-cal" or a "no-cal" mode than are purely linear methods.

Here, the "no-cal" mode is, as its name implies, simply a mode of operation of the invention in which no empirically determined, patient-specific value of $k_r$ is supplied at all. This would eliminate the need for external calibration. In such cases, $k_r$ could be set either simply to unity, or it could be set to an value pre-determined experimentally on, for example, a representative population of subjects, or of a population of subjects representative in some way (such as with respect to age, weight, sex, pathology, etc.) of the current subject/patient.

Another advantage of the invention is that a benefit of the square-root error dependence is that it is possible to use an averaged calibration constant for a whole population under study. For example, in tests, the inventors were able to use a $k_r$ value of 1.4, and yet were able to keep the DC-shift (offset) error under 30% for 85% of the patients. Also, the inventors also propose that noninvasive methods such as ECG and bioimpedance may be used to estimate $k_r$; even in such cases, the recursive nature of the invention makes it more appropriate than prior art systems, since it is less sensitive to any error in the calibration constant estimation.

Advantages

The invention displays several advantages over the prior art. Some advantages are mentioned above; others include:

a) High accuracy: Results on animal and clinical radial and femoral data show that the invention offers significantly higher accuracy when compared with competing devices.

b) Improved trending: Results on animal radial and femoral data show that changes in the peripheral resistance, for example after vasodilation or vasoconstriction, are well reflected in the estimated CO trends.

c) The invention may be used in a "no-cal" mode, that is, with no a priori value of the calibration constant $k_r$ available.

d) In the "no-cal" mode, the invention works well even if an average calibration constant is used (within 30% error in 85% of the cases). The accuracy of the "no-cal" mode of the invention can be improved, however, if the calibration constant $k_r$ is estimated using a third parameter: In an animal study, the inventors were able to show that the slope of the rising edge of the blood pressure waveform can be used to group the animals by their calibration constants. The inventors propose that this technique may also be used on humans, such that the calibration constant of each patient's group is used for that patient according to the characteristics of the group, such as age, body mass, sex, etc., that is, standard anthropometric characteristics. Also, a third measurement could be used to estimate the calibration constant; this measurement could be based on different techniques, such as EKG (QRS—Systole onset interval) and bioimpedance (Volume—Compliance relation).

e) The method according to the invention is computationally simpler than other existing pulse contour methods. For example, there is no need to detect the dicrotic notch in the blood pressure waveform, which makes the invention more stable and less sensitive to errors, noise and motion artifacts.

f) The invention is able to estimate peripheral resistance R directly, with no need to derive it indirectly from the decay constant $\tau$. This is a useful property in applications that estimate cardiovascular parameters other than, or in addition to CO, based on R. Indeed, since R has clinical significance of its own, the aspects of the invention described above relating to the estimation of R may be all that are needed in some cases.

System Components

Figure 9:
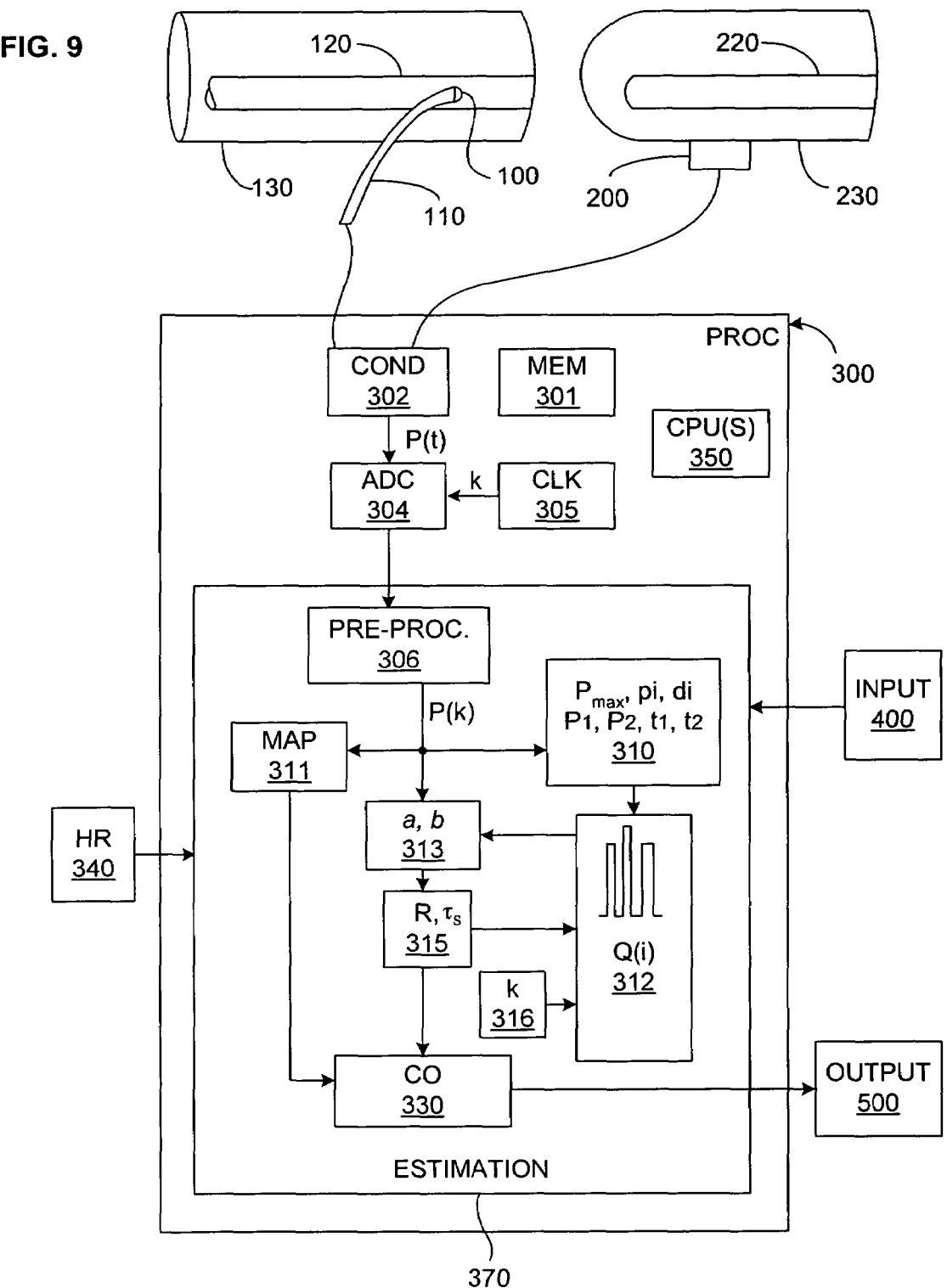
FIG. 9 is a block diagram showing the main components of a system according to the invention.

FIG. 9 shows the main components of a system that implements the method described above for sensing pressure and calculating CO according to the invention. The invention may be included within an existing patient-monitoring device, or it may be implemented as a dedicated monitor. As is mentioned above, pressure, or some other input signal proportional to pressure, may be sensed in either or, indeed, both, of two ways: invasively and non-invasively. Simply because it is anticipated to be the most common implementation of the invention, the system is described as measuring arterial blood pressure as opposed to some other input signal that is converted to pressure.

FIG. 9 shows both types of pressure sensing for the sake of conciseness; in most practical applications of the invention, either one or several variations will typically be implemented. In invasive applications of the invention, a conventional pressure sensor 100 is mounted on a catheter 110, which is inserted in an artery 120 of a portion 130 of the body of a human or animal patient. Such artery could be an ascending aorta, or pulmonary artery, or, in order to reduce the level of invasiveness, the artery 120 could be peripheral, such as the femoral, radial or brachial artery. In the non-invasive applications of the invention, a conventional pressure sensor 200, such as a photo-plethysmographic blood pressure probe, is mounted externally in any conventional manner, for example using a cuff around a finger 230 or a transducer mounted on the wrist of the patient. FIG. 9 schematically shows both types.

The signals from the sensors 100, 200 are passed via any known connectors as inputs to a processing system 300, which includes one or more processors 350 and other supporting hardware, such as a memory 301, and system software (not shown) usually included to process signals and execute code. The invention may be implemented using a modified, standard, personal computer, or it may be incorporated into a larger, specialized monitoring system. In this invention, the processing system 300 also may include, or is connected to, conditioning circuitry 302 which performs such normal signal processing tasks as amplification, filtering, ranging, etc., as needed.

The conditioned, sensed input pressure signal P(t) is then converted to digital form by a conventional analog-to-digital converter ADC 304, which has or takes its time reference from a clock circuit 305. As is well understood, the sampling frequency of the ADC 304 should be chosen with regard to the Nyquist criterion so as to avoid aliasing of the pressure signal; this procedure is very well known in the art of digital signal processing. The output from the ADC 304 will be a discrete representation of the pressure signal P(t), whose sampled values may be stored in conventional memory circuitry (not shown).

A signal pre-processing module 306 is preferably included, with routines to provide such known pre-processing as digital filtering for general (as opposed to interval-to-interval) noise removal, for motion artifact rejection, pulse beat detection (if needed), for rejection of bad beats, etc. This module may also be implemented wholly or partially in hardware. Known circuitry may be included to indicate, for example, that signal strength is too low, and that the delivered measurement values are unreliable. As such, the module 306 may also be located functionally, wholly or partially, before the ADC 304. The output from the module 306 is shown as P(k), since, if the pre-processing module 306 is included at all its values will form the data set corresponding to pressure that is used in the computations described above.

The values P(k) are passed (usually, accessed from memory by) to a software module 310 comprising computer-executable code for determining the pressure and time parameters used in the computations for the chosen model. For the two-element model described above, these will be the maximum pressure value $P_{max}$, pi and di; for the three-element model, P1, P2, t1 and t2 are determined.

Yet another module 311 computes the mean arterial pressure MAP over the chosen computation interval such as a cardiac cycle, which may be triggered by any known hardware device and/or software routine 340 that detects heart rate or at least signals the beginning of a cardiac cycle. Note that the embodiments of the invention described above do not strictly require any information about the beginning and end of pressure waveforms during a computation interval other that what can be derived from the pressure waveforms themselves. The heart rate monitoring routine or device is therefore optional, although it may be helpful as a way to check that the pressure waveforms are correctly delimited.

Once the values of $P_{max}$, pi and di are available from the current pressure waveform, that is, for the current cardiac cycle, the corresponding current assumed input waveform component Q(i,k) can be generated as described above and added to the train of assumed input waveform components. A module 312 is illustrated in FIG. 9 that generates the assumed input waveform components.

A system parameter identification module 313 takes the discrete pressure waveform P(k) and the train of assumed input waveform components Q(i) as inputs. As described above, this module computes the coefficients a and b that over each cardiac cycle, yield a transfer function that best generates the observed pressure signal P(t) in any chosen sense, such as least squares.

Once the coefficients a and b are computed, they are passed as input parameters to another module 315, which calculates a value of R and, depending on the implemented embodiment, also $\tau_s$. The value of R (and of $\tau_s$ if needed) is passed both to the assumed input waveform component generation (or, more generally, the input flow waveform) module 312, and to another module 330 that performs the calculations indicated above for computing the cardiovascular value of interest, such as a CO value, a value that is derived from CO, etc. Yet another module 316—which will in most cases simply be a memory position—provides to the module 312 the calibration constant $k_r$, which may be determined as described above.

Software modules 310, 311, 312, 313, 315, 316 and 330 can be programmed using known techniques. Of course, any or all of these modules may be combined, even into a single body of code; they are shown separately for the sake of clarity. Indeed, any or all of the illustrated modules may be implemented simply as routines within a single estimation software component 370, which may of course be combined with other software components of the processing system 300 as desired. Moreover, any or all of the software components of the invention may also be stored as computer-executable instructions on any form of computer-readable medium (CD ROM, memory or disk space made available for downloading, etc.) for loading into and execution by different processing systems.

Once a CO estimate has been computed, it is passed to any desired output device 500, such as a user-viewable monitor, and displayed, stored or transmitted in any chosen format. An input device 400 is preferably also included to allow the user to input, for example, the calibration constant $k_r$, administrative and patient-specific information, to adjust the display, to choose the computation interval, etc.

Dynamically Constructed Assumed Flow Input Waveforms

It has been mentioned above that the assumed input flow waveform Q(i) need not be a square wave, but rather could be some other shape whose amplitude and duration are adjusted according to the current pressure waveform. It would also be possible to posit, for each pressure cycle, an input flow waveform whose shape is more generally adjustable, with shape parameters that are determined as part of the optimization inherent in the system identification procedure. In other words, parameters defining the shape of each assumed input waveform component could be included, along with the parameters defining the model of the relationship (such as the transform function) between the assumed input flow waveform and the current pressure waveform data set, as optimization parameters of a single identification routine. The parameters of both may then be determined simultaneously to yield both an optimal assumed input flow waveform and an optimal model as defined according to any chosen metric, such as least squares.

The approximate shape of a typical beat-to-beat flow profile is known. See, for example, box 50 in FIG. 5, which illustrates a characteristic flow waveform. As just one example, an initial "generic" flow waveform Q(i,0) could be defined as a discrete (sampled) representation of the parabola $$Q(t) = c2*x^2 + c1*x + c0$$

where $x = [t - (t_{sys} - \text{offset})]$, that is, time measured relative to the time of maximum pressure. The parameters c2 (which will usually be negative), c1, c0 and even offset could then be included as four of six optimization parameters in the system identification routine used also to estimate optimal a and b values in the transfer function model.

The result of the numerical optimization will then be parameters defining not only optimal a and b values, but also the parameters defining an optimal parabolic approximation of the input flow waveform. In other words, by relaxing the assumption of a fixed flow waveform shape (such as square-wave with a duration and amplitude defined before system identification) even further, the invention would thus determine not only which transfer function but also which input waveform (not necessarily parabolic) most likely (in the sense of any chosen metric, such as least squares) has led to the observed pressure waveform. Integrating over the approximated input flow waveform may then provide an estimate of total flow over the pressure cycle.

Other approximating functions for input flow could of course also be determined in this manner. For example, a higher order polynomial could be used. As yet another example, the initial input flow waveform could be assumed to be a set of Bezier curves, such that the positions of each curve's two endpoints and two control points (for a total of eight optimization parameters per curve) could be made parameters that are computed in the optimization step of the system identification routine. Yet another example would be the amplitudes of component sine waves pre-determined initially through Fourier analysis of representative, actually measured input flow waveforms. Still other approximating functions will of course occur to those skilled in the art of system identification and reconstruction techniques.

It would even be possible to use the method according to the invention primarily to determine an optimal functional approximation of flow: Assume that one has in some other way (or even using the invention over earlier cycles) determined the parameters defining the transfer function model of the pressure response P(t) to input flow Q(t). For example, one may have determined the parameters of an n-element aortic Windkessel model that one assumes to be accurate enough. The parameters defining the general shape (such as polynomial, sinusoidal, piecewise linear, etc.) of an assumed input flow could then be optimized using the system-identification procedure described above. For each cycle or group of cycles, the specific shape of an optimum input flow model (that is, function) would then be determined even without simultaneous optimization or adjustment of any transfer function model coefficients at all. Cardiac flow may then be estimated from the assumed input flow waveform, either directly or possibly after scaling; any needed scaling may be determined using known methods.

Knowledge of a flow model may be useful in its own right, but may also be combined with other information to provide other diagnostic indicators. For example, integrating the assumed input flow waveform over a cardiac cycle will yield an estimate of cardiac stroke volume (SV). Note that this estimate of SV does not require knowledge of arterial diameter or cross-sectional area as many other SV-estimating systems do.

We claim:

1. A method for determining a cardiovascular parameter equal to or derivable from cardiac output (CO) comprising:
    inputting a current pressure waveform data set corresponding to arterial blood pressure over a current pressure cycle;
    determining defining parameters of an assumed input flow waveform as a function of a peripheral resistance value determined for at least one previous pressure cycle;
    determining model parameters of a model of a relationship between the assumed input flow waveform and the current pressure waveform data set;
    computing a current peripheral resistance value as a function of the model parameters; and
    computing an estimate of the cardiovascular parameter as a function of the current peripheral resistance value and the current pressure waveform data set.

2. A method as in claim 1, further comprising determining the defining parameters of the assumed input flow waveform also as a function of shape characteristics of the current pressure waveform data set.

3. A method as in claim 2, in which the assumed input flow waveform is a series of component waveforms, with one component waveform per pressure cycle.

4. A method as in claim 3, in which:
    the defining parameters include duration and amplitude; and
    the duration of the component waveform for the current pressure cycle is set at least approximately equal to a time interval between systole onset and systole in the current pressure waveform data set.

5. A method as in claim 4, further comprising:
    estimating a diastolic time constant as a product of a sampling rate at which the pressure waveform data set is derived and a function of a model feedback parameter;
    estimating an arterial compliance value as a ratio of the diastolic time constant and the peripheral resistance value;
    estimating a systolic time constant from chosen points in the current pressure waveform data set;
    computing an aortic characteristic resistance value as a ratio of the systolic time constant and the arterial compliance value;

setting the amplitude of the component waveform for the current pressure cycle to be inversely proportional to the square of a function of at least one aortic characteristic resistance value.

6. A method as in claim 5, further comprising:
computing the mean of a plurality of aortic characteristic resistance values, which will include at least one aortic characteristic resistance value estimated for a previous cycle;
setting the amplitude of the component waveform for the current pressure cycle to be inversely proportional to the square of the product of the mean and a calibration constant.

7. A method as in claim 6, further comprising setting the amplitude of the component waveform for the current pressure cycle to be inversely proportional to the square of the product of the mean, the calibration constant, and the arterial compliance value.

8. A method as in claim 3, in which the assumed input flow waveform comprises a train of square-wave signals, each forming a respective one of the component waveforms.

9. A method as in claim 3, further comprising:
setting the amplitude of the component waveform for the current pressure cycle to be proportional to a peak-to-peak value of the current pressure waveform data set and inversely proportional to a function of the current peripheral resistance value.

10. A method as in claim 9, further comprising:
determining a mean value of a plurality of previously estimated peripheral resistance values; and
setting the amplitude of the component waveform for the current pressure cycle to be proportional to the peak-to-peak value and inversely proportional to the mean value.

11. A method as in claim 10, further comprising:
determining a calibration constant; and
setting the amplitude of the component waveform for the current pressure cycle to be proportional to the peak-to-peak value and inversely proportional to the mean value scaled by the calibration constant.

12. A method as in claim 1, in which:
the model is a discrete, auto-regressive representation of a multi-element Windkessel model of the aorta; and
the model parameters are coefficients of the discrete, auto-regressive representation.

13. A system for determining a cardiovascular value equal to or derivable from cardiac output (CO) comprising:
an arrangement generating a current pressure waveform data set corresponding to arterial blood pressure over a current pressure cycle;
a processing system including:
an input flow waveform generation module comprising computer-executable code for determining defining parameters of an assumed input flow waveform as a function of a peripheral resistance value determined for at least one previous pressure cycle;
a system parameter identification module comprising computer-executable code for determining model parameters of a model of a relationship between the assumed input flow waveform and the current pressure waveform data set;
a model parameter computation module comprising computer-executable code for computing a current peripheral resistance value as a function of the model parameters; and
a cardiovascular value computation module comprising computer-executable code for computing an estimate of the cardiovascular parameter as a function of the current peripheral resistance value and the current pressure waveform data set.

14. A system as in claim 13, in which the system parameter identification module is further provided with computer-executable code for determining the defining parameters of the assumed input flow waveform also as a function of shape characteristics of the current pressure waveform data set.

15. A system as in claim 14, in which the assumed input flow waveform is a series of component waveforms, with one component waveform per pressure cycle.

16. A system as in claim 15, in which:
the defining parameters include duration and amplitude; and
the duration of the component waveform for the current pressure cycle is set at least approximately equal to a time interval between systole onset and systole in the current pressure waveform data set.

17. A system as in claim 15, in which the input flow waveform generation module is further provided for setting the amplitude of the component waveform for the current pressure cycle to be proportional to a peak-to-peak value of the current pressure waveform data set and inversely proportional to a function of the current peripheral resistance value.

18. A system as in claim 17, further comprising:
an averaging module comprising computer-executable code for determining a mean value of a plurality of previously estimated peripheral resistance values;
in which input flow waveform generation module is further provided for setting the amplitude of the component waveform for the current pressure cycle to be proportional to the peak-to-peak value and inversely proportional to the mean value.

19. A system as in claim 18, further comprising:
a calibration module determining a calibration constant;
in which the input flow waveform generation module is further provided for setting the amplitude of the component waveform for the current pressure cycle to be proportional to the peak-to-peak value and inversely proportional to the mean value scaled by the calibration constant.

20. A system as in claim 16, in which the assumed input flow waveform is a train of square-wave signals, each forming a respective one of the component waveforms.

21. A system as in claim 13, in which:
the model is a discrete, auto-regressive representation of a multi-element Windkessel model of the aorta; and
the model parameters are coefficients of the discrete, auto-regressive representation.

* * * * *